(12) United States Patent
Wilson et al.

(10) Patent No.: US 6,962,649 B2
(45) Date of Patent: *Nov. 8, 2005

(54) CONTACT ASSEMBLIES, METHODS FOR MAKING CONTACT ASSEMBLIES, AND MACHINES WITH CONTACT ASSEMBLIES FOR ELECTROCHEMICAL PROCESSING OF MICROELECTRONIC WORKPIECES

(75) Inventors: Gregory J. Wilson, Kalispell, MT (US); John M. Pedersen, Kalispell, MT (US); Steve L. Eudy, Kalispell, MT (US)

(73) Assignee: Semitool, Inc., Kalispell, MT (US)

( * ) Notice: Subject to any disclaimer, the term of this patent is extended or adjusted under 35 U.S.C. 154(b) by 213 days.

This patent is subject to a terminal disclaimer.

(21) Appl. No.: 10/008,636

(22) Filed: Dec. 5, 2001

(65) Prior Publication Data

US 2003/0141185 A1 Jul. 31, 2003

(Under 37 CFR 1.47)

Related U.S. Application Data

(63) Continuation-in-part of application No. 09/717,927, filed on Nov. 20, 2000, now Pat. No. 6,527,925, which is a continuation-in-part of application No. 09/113,723, filed on Jul. 10, 1998, now Pat. No. 6,080,291.

(51) Int. Cl.[7] ............................................. C25D 17/00
(52) U.S. Cl. ................ 204/224 R; 204/280; 204/286.1; 204/297.01; 204/297.06; 204/297.07; 204/297.08; 204/297.09; 204/297.1; 204/297.14
(58) Field of Search ............................ 204/224 R, 280, 204/286.1, 297.01, 297.06, 297.08, 297.09, 297.1, 297.14, 297.07

(56) References Cited

U.S. PATENT DOCUMENTS

| | | | | |
|---|---|---|---|---|
| 5,522,975 | A | * | 6/1996 | Andricacos et al. ...... 204/288.1 |
| 5,833,820 | A | * | 11/1998 | Dubin ........................ 204/212 |
| 5,909,123 | A | | 6/1999 | Budnaitis |
| 6,080,289 | A | * | 6/2000 | Palmatier et al. ........... 204/242 |
| 6,228,231 | B1 | * | 5/2001 | Uzoh ..................... 204/224 R |
| 6,251,236 | B1 | * | 6/2001 | Stevens .................. 204/224 R |
| 6,303,010 | B1 | | 10/2001 | Woodruff et al. |
| 6,309,520 | B1 | | 10/2001 | Woodruff et al. |
| 6,326,587 | B1 | | 12/2001 | Cardineau |
| 6,334,937 | B1 | | 1/2002 | Batz, Jr. et al. |

OTHER PUBLICATIONS

International Search Report for PCT/US02/39244; Applicant Semitool, Inc.; Mar. 18, 2003; 7 pgs.

* cited by examiner

*Primary Examiner*—Arun S. Phasge
(74) *Attorney, Agent, or Firm*—Perkins Coie LLP

(57) ABSTRACT

Contact assemblies for electrochemical processing of microelectronic workpieces. The contact assemblies can comprise a support member that includes an inner wall which defines an opening configured to receive the workpiece and a plurality of contacts. The individual contacts include a conductor and a cover. The conductor can comprise a proximal section projecting inwardly into the opening relative to the support member, a distal section extending from the proximal section, and an inert exterior at least at the distal section. The cover comprises a dielectric element that covers at least the proximal section of the conductor, but does not cover at least a portion of the distal section of the core. The exposed portion of the distal section of the core, accordingly, defines a conductive contact site for contacting a conductive layer (e.g., a seed layer) on the workpiece.

44 Claims, 12 Drawing Sheets

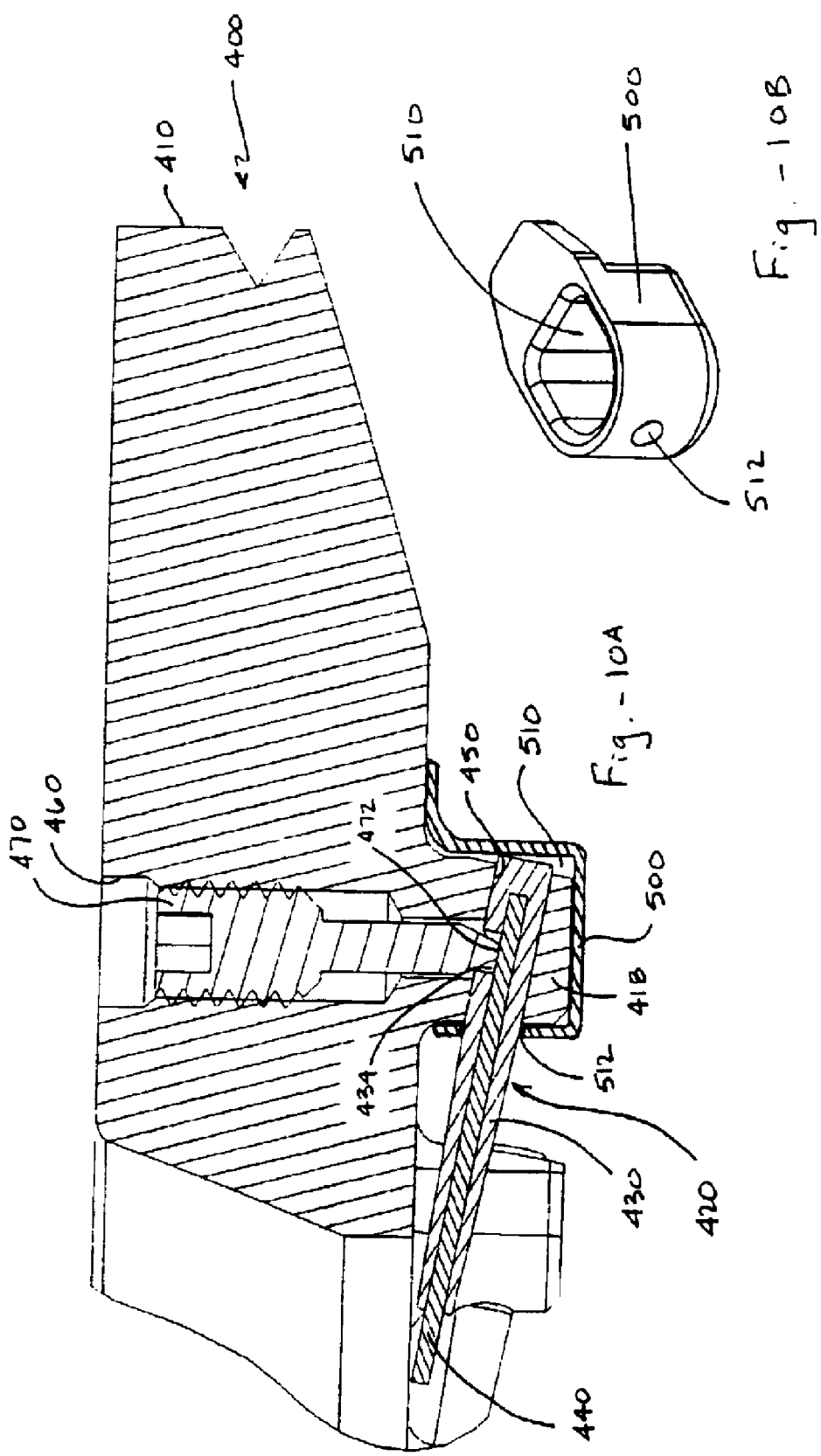

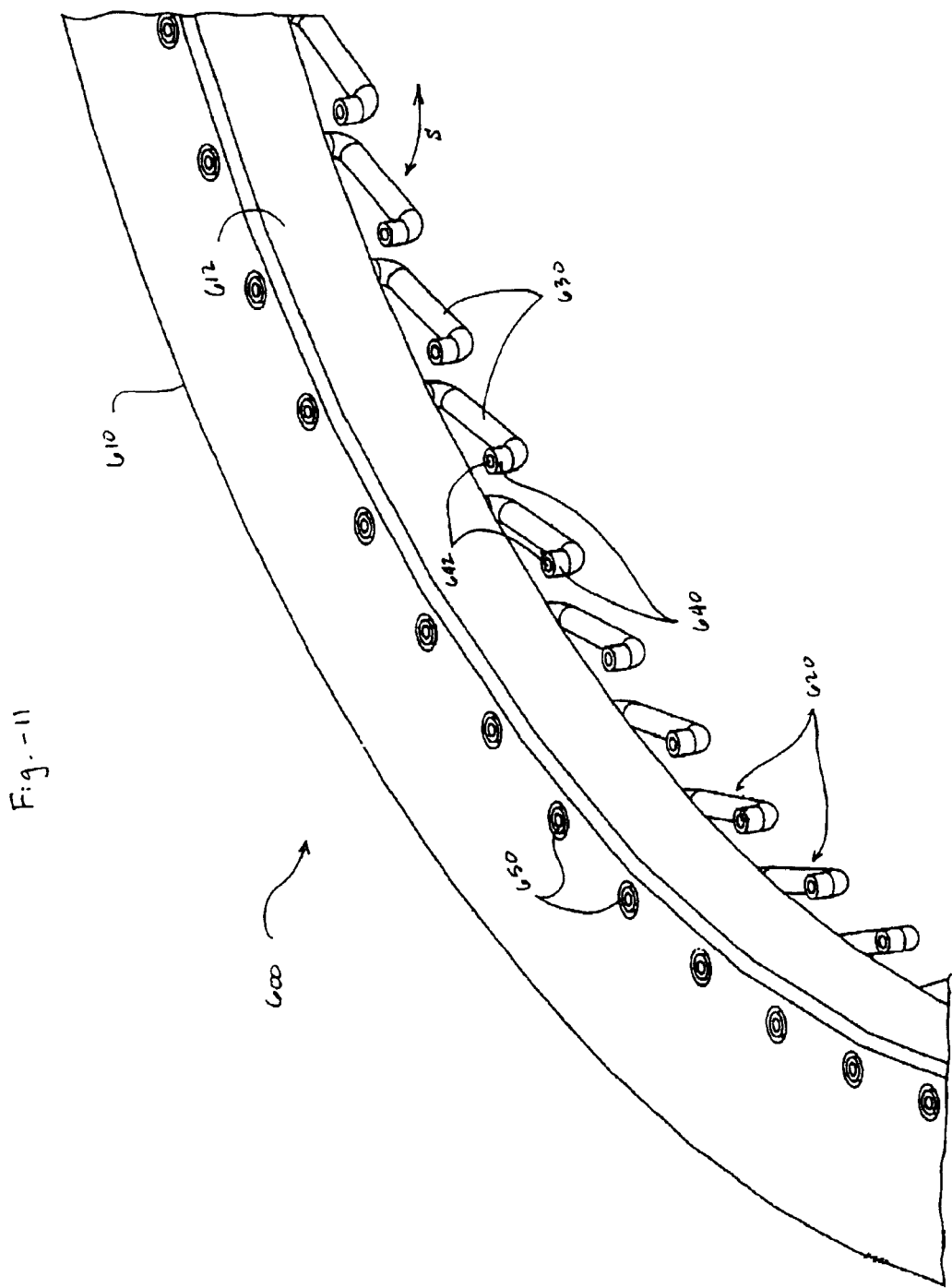

CONTACT ASSEMBLIES, METHODS FOR MAKING CONTACT ASSEMBLIES, AND MACHINES WITH CONTACT ASSEMBLIES FOR ELECTROCHEMICAL PROCESSING OF MICROELECTRONIC WORKPIECES

CROSS-REFERENCE TO RELATED APPLICATION(S)

The present application is U.S. patent application Ser. No. 09/717,927, filed Nov. 20, 2000 U.S. Pat. No. 6,527,925, which is continuation-in-part of U.S. application Ser. No. 09/113,723, filed Jul. 10 1998 U.S. Pat. No. 6,080,291. All of the foregoing applications are herein incorporated by reference in their entirety.

TECHNICAL FIELD

The following disclosure is related to contact assemblies for providing an electrical potential to a microelectronic workpiece for electrochemical processing of the workpiece.

BACKGROUND

Microelectronic devices, such as semiconductor devices and field emission displays, are generally fabricated on and/or in microelectronic workpieces using several different types of machines ("tools"). Many such processing machines have a single processing station that performs one or more procedures on the workpieces. Other processing machines have a plurality of processing stations that perform a series of different procedures on individual workpieces or batches of workpieces. In a typical fabrication process, one or more layers of conductive materials are formed on the workpieces during deposition stages. The workpieces are then typically subject to etching and/or polishing procedures (i.e., planarization) to remove a portion of the deposited conductive layers for forming electrically isolated contacts and/or conductive lines.

Plating tools that plate metals or other materials on the workpieces are becoming an increasingly useful type of processing machine. Electroplating and electroless plating techniques can be used to deposit nickel, copper, solder, permalloy, gold, silver, platinum and other metals onto workpieces for forming blanket layers or patterned layers. A typical metal plating process involves depositing a seed layer onto the surface of the workpiece using chemical vapor deposition (CVD), physical vapor deposition (PVD), electroless plating processes, or other suitable methods. After forming the seed layer, a blanket layer or patterned layer of metal is plated onto the workpiece by applying an appropriate electrical potential between the seed layer and an electrode in the presence of an electroprocessing solution. The workpiece is then cleaned, etched and/or annealed in subsequent procedures before transferring the workpiece to another processing machine.

FIG. 1A illustrates an embodiment of a single-wafer processing station 1 that includes a container 2 for receiving a flow of electroplating solution from a fluid inlet 3 at a lower portion of the container 2. The processing station 1 can include an anode 4, a plate-type diffuser 6 having a plurality of apertures 7, and a workpiece holder 9 for carrying a workpiece 5. The workpiece holder 9 can include a contact assembly having a plurality of electrical contacts for providing electrical current to a seed layer on the surface of the workpiece 5. The seed layer acts as a cathode when it is biased with a negative potential relative to the anode 4. The electroplating fluid flows around the anode 4, through the apertures 7 in the diffuser 6, and against the plating surface of the workpiece 5. The electroplating solution is an electrolyte that conducts electrical current between the anode 4 and the cathodic seed layer on the surface of the workpiece 5. Therefore, ions in the electroplating solution plate onto the surface of the workpiece 5.

The plating machines used in fabricating microelectronic devices must meet many specific performance criteria. For example, many processes must be able to form small contacts in vias that are less than 0.5 $\mu$m wide, and are desirably less than 0.1 $\mu$m wide. The plated metal layers accordingly often need to fill vias or trenches that are on the order of 0.1 $\mu$m wide, and the layer of plated material should also be deposited to a desired, uniform thickness across the surface of the workpiece 5.

The structure of the contact assembly can significantly influence the uniformity of the plated metal layer because the plating rate across the surface of the microelectronic workpiece is influenced by the distribution of the electrical current (the "current density") across the seed-layer. One factor that affects the current density is the distribution of the electrical contacts around the perimeter of the workpiece. In general, a large number of discrete electrical contacts should contact the seed-layer proximate to the perimeter of the workpiece to provide a uniform distribution of current around the perimeter of the workpiece. Another factor that affects the current density is the formation of oxides on the seed-layer. Oxides are generally resistive, and thus oxides reduce the efficacy of the electrical connection between the contacts and the seed-layer. Still other factors that can influence the current density are (a) galvanic etching between the contacts and the seed-layer, (b) "theiving" of material near the contacts caused by plating on the contacts during a plating cycle, (c) gas bubbles on the seed-layer, and (d) other aspects of electroplating that affect the quality of the connection between the contacts and the seed-layer or the fluid dynamics at the surface of the workpiece. The design of the contact assembly should address these factors to consistently provide a desired current density across the workpiece.

One type of contact assembly is a "dry-contact" assembly having a plurality of electrical contacts that are sealed from the electroplating solution. For example, U.S. Pat. No. 5,227,041 issued to Brogden et al. discloses a dry contact electroplating structure having a base member for immersion into an electroplating solution, a seal ring positioned adjacent to an aperture in the base member, a plurality of contacts arranged in a circle around the seal ring, and a lid that attaches to the base member. In operation, a workpiece is placed in the base member so that the front face of the workpiece engages the contacts and the seal ring. When the front face of the workpiece is immersed in the electroplating solution, the seal ring prevents the electroplating solution from contacting the contacts inside the base member. Other types of dry contact assemblies are disclosed in U.S. Pat. Nos. 6,139,712, and 6,309,524.

One manufacturing concern of dry-contact assemblies is that galvanic etching occurs between the contacts and the seed-layer when an electrolyte solution gets into the dry contact area. Galvanic etching removes the seed-layer at the interface of the contacts, which can cause a non-uniform current distribution around the perimeter of the workpiece. Therefore, even though dry-contact assemblies keep the contacts clean, they may produce non-uniform metal layers on the workpieces.

Another type of contact assembly is a "wet-contact" assembly having a plurality of electrical contacts that are exposed to the electroplating solution during a plating cycle. Because the contacts are exposed to the electroplating solution during a plating cycle, the metal in the electroplating solution also plates onto the contacts. The contacts, however, may plate at different rates such that some contacts can have a greater surface area of conductive material contacting the seed-layer. The in-situ plating of contacts can accordingly reduce the uniformity of the metal layer on the workpiece. Additionally, wet-contact assemblies must be periodically "de-plated" to remove the metal that plates onto the contacts during a plating cycle.

To overcome these shortcomings, the parent patent application (U.S. application Ser. No. 09/717,927) discloses several embodiments of wet-contact assemblies that have contact members with a conductive finger, a dielectric coating on the finger, and a conductive contact site exposed through an opening in the dielectric coating. FIG. 1B is a cross-sectional view of a contact member 20 comprising a biasing element 21 having a raised feature 22 at a contact site 23 in accordance with one embodiment of the contact assembly as disclosed in U.S. application Ser. No. 09/717,927. The biasing element 21 can be a finger made from titanium or another suitable conductive material, and it can be coated with a conductive contact layer 24 which is itself coated with a dielectric coating 25. A portion of the dielectric coating 25 is removed from the contact site 23 to form a opening or aperture 26 that exposes the conductive contact layer 24. The aperture 26 can be formed using laser ablation or etching techniques. FIG. 1C illustrates an alternate embodiment of a contact member 30 disclosed in U.S. application Ser. No. 09/717,927 that has a biasing element 31, a dielectric layer 32, and a conductive contact material 33 in an opening 34 of the dielectric layer 32. The opening 34 can be formed in the dielectric layer 32, and then a mass of the conductive contact material 33 can be deposited into the opening 34 to form a bump. The embodiments of wet-contact assemblies disclosed in U.S. application Ser. No. 09/717,927 are included in this section solely for background information, and thus they are not admitted prior art to the present application.

The wet-contact assemblies disclosed in U.S. application Ser. No. 09/717,927 provide a significant improvement over the art, but they are difficult to manufacture because they involve precise etching and machining processes to form contact sites having an inert contact material. The wet-contact assemblies disclosed in U.S. application Ser. No. 09/717,927 may also have relatively short life spans because (a) thin dielectric coatings on the contact members may crack causing uncontrolled theiving, (b) the contact sites may wear down causing uncontrolled corrosion and oxidation that produces non-uniformities in the plated layer, and (c) the contact material may separate from the underlying material because of a lack of adhesion. For example, a layer of platinum at the contact site may wear down quickly or flake away because de-plating of the contacts after every plating cycle affects the interface between the platinum contact material and the underlying titanium finger. Thus, even though the wet-contact assemblies disclosed in U.S. application Ser. No. 09/717,927 are highly useful, it would be desirable to develop less expensive wet-contact assemblies that last longer.

SUMMARY

The present invention is directed toward contact assemblies, reactors that use contact assemblies, and integrated plating machines for electrochemical processing of microelectronic workpieces. Several embodiments of contact assemblies in accordance with the invention provide inexpensive, durable contacts for wet-contact systems. The contact assemblies in accordance with the invention are expected to provide highly robust contact sites that can withstand de-plating cycles and rubbing against the workpieces. Many embodiments of the contacts are thus expected to enhance the ability to accurately plate or de-plate material from a workpiece for a long life cycle. Many of the embodiments of the invention are also expected to provide these benefits while also being relatively inexpensive to manufacture and maintain.

One embodiment of the invention is a contact assembly comprising a support member and a plurality of contacts. The support member includes an inner wall that defines an opening configured to receive the workpiece. The individual contacts include a conductor and a cover. The conductor comprises a proximal section projecting inwardly into the opening relative to the support member, a distal section extending from the proximal section, and an inert exterior at least at the distal section. The inert exterior is a material that is electrically conductive, but resists being consumed by the electrolytic processing solution in the presence of an electrical field. The conductor, for example, can be a platinum rod, a titanium rod coated with a thin platinum layer, a stainless steel rod, a tungsten rod, or other materials that are inert in the particular type of electrolytic processing solution. The cover comprises a dielectric element that covers at least the proximal section of the conductor, but does not cover at least a portion of the distal section of the core. The exposed portion of the distal section of the core, accordingly, defines a conductive contact site for contacting a conductive layer (e.g., a seed layer) on the workpiece.

Several embodiments of contact assemblies in accordance with the invention are robust and have long life spans because the conductors are a rod of an inert material as opposed to a thin layer of inert material plated onto a consumable material. As a result, even though the distal sections of the conductors may wear down because of abrasion against the wafer or de-plating, they are not as subject to corrosion or flaking as a thin plated layer. This enhances the life span of the contact assemblies. Additionally, several embodiments of the contact assemblies are inexpensive to manufacture because the cover can be a dielectric sheath, and the contacts can be made by simply inserting a small rod of inert material into the bore of a dielectric sheath or. molding a dielectric sheath around an inert rod. This is much less expensive than laser machining or etching an aperture in a thin dielectric layer without removing an underlying platinum layer and/or depositing a small platinum bump into a hole in a dielectric layer. Therefore, several embodiments of contact assemblies in accordance with the present invention provide inexpensive, durable contacts for wet-contact systems that can be used for electrochemical processing of microelectronic workpieces.

BRIEF DESCRIPTION OF THE DRAWINGS

FIG. 10A is a partial cross-sectional view of a contact assembly in accordance with another embodiment of the invention.

FIG. 10B is a top isometric view of a boot for the contact assembly of FIG. 10A.

FIG. 11 is a top isometric view of another contact assembly in accordance with still another embodiment of the invention.

DETAILED DESCRIPTION

The following description discloses the details and features of several embodiments of contact assemblies, electrochemical processing reactors, and integrated tools to process microelectronic workpieces. The term "microelectronic workpiece" is used throughout to include a workpiece formed from a substrate upon which and/or in which microelectronic circuits or components, data storage elements or layers, and/or micro-mechanical elements are fabricated. It will be appreciated that several of the details set forth below are provided to describe the following embodiments in a manner sufficient to enable a person skilled in the art to make and use the disclosed embodiments. Several of the details and advantages described below, however, may not be necessary to practice certain embodiments of the invention. Additionally, the invention can include additional embodiments that are within the scope of the claims, but are not described in detail with respect to FIGS. 2–11.

The operation and features of the contact assemblies are best understood in light of the environment and equipment in which they can be used to electrochemically process workpieces (e.g., electroplate and/or electropolish). As such, embodiments of integrated tools and reactors in which the contact assemblies can be used are initially described with reference to FIGS. 2 and 3. The details and features of several embodiments of contact assemblies and contacts are then described with reference to FIGS. 4–11.

Figure 1A:
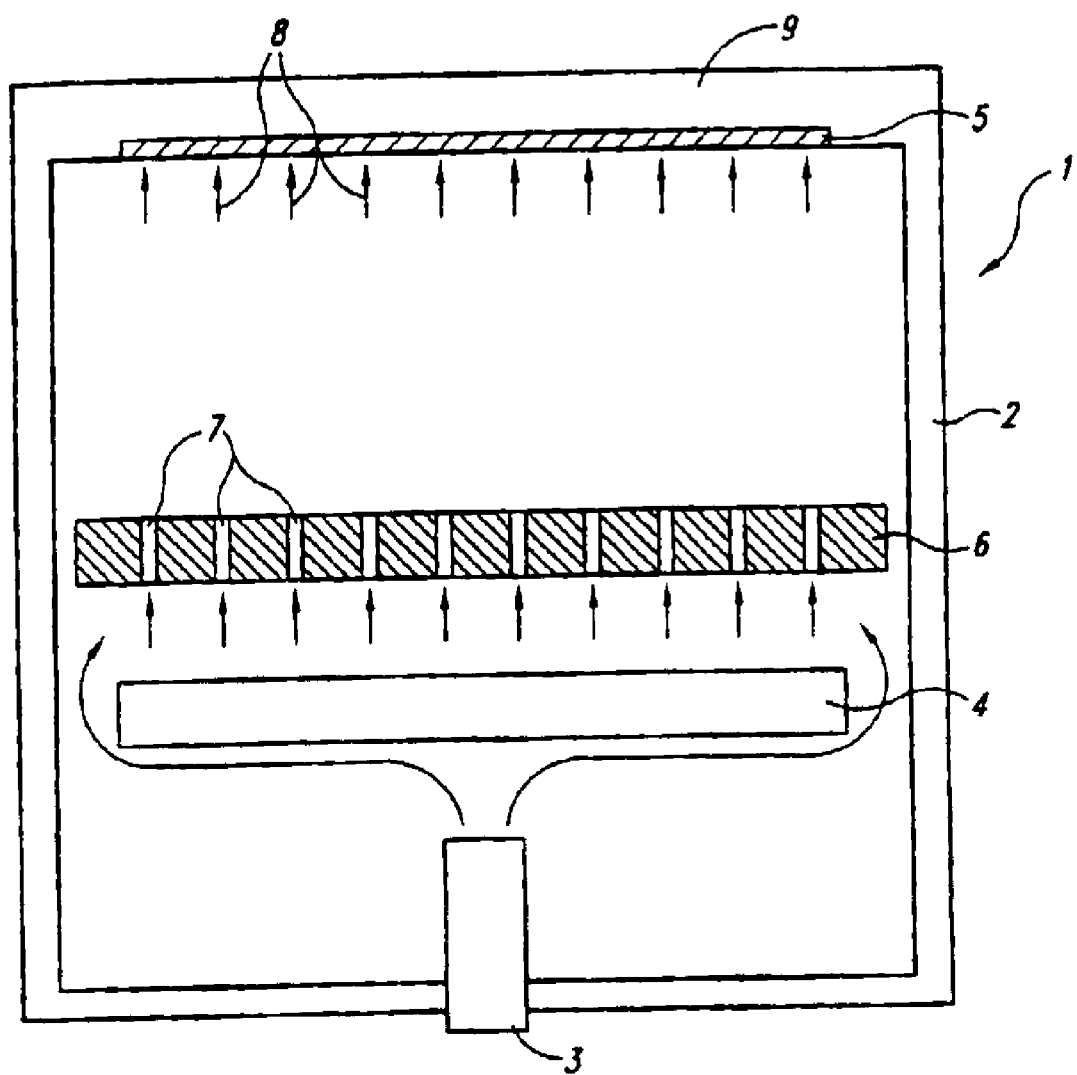
FIG. 1A is a schematic diagram of an electroplating chamber in accordance with the prior art.
Figure 1B:
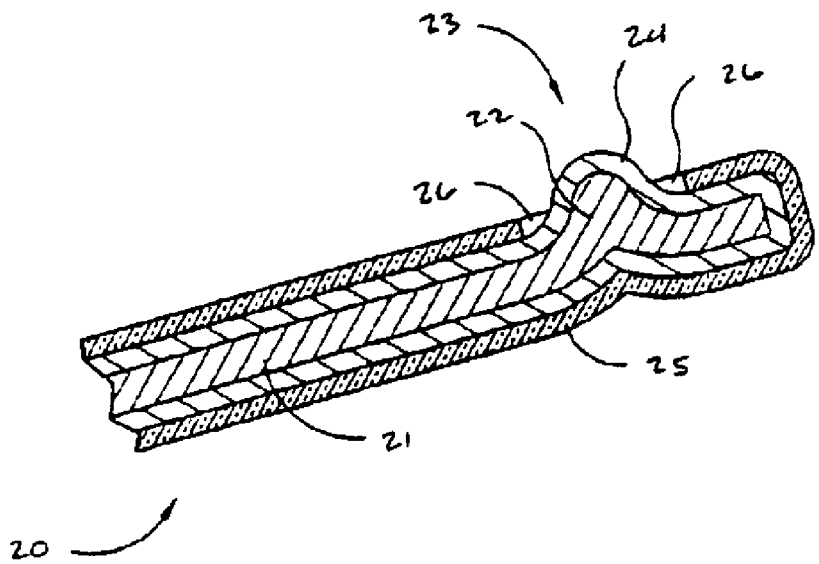
FIG. 1B is a cross-sectional view of a contact member in accordance with an embodiment of the parent application. This contact member is disclosed herein as background information and is expressly omitted as being admitted prior art.
Figure 1C:
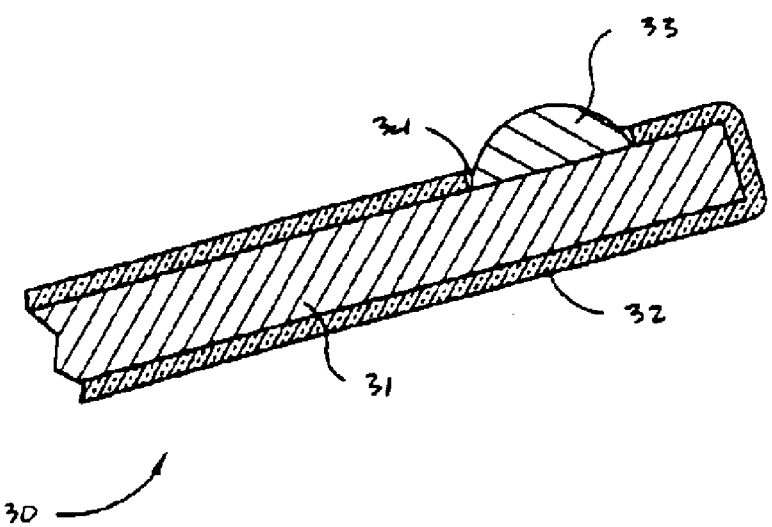
FIG. 1C is a cross-sectional view of a contact member in accordance with another embodiment of the parent application. This contact is disclosed herein as background information and is expressly omitted as being admitted prior art.
Figure 2:
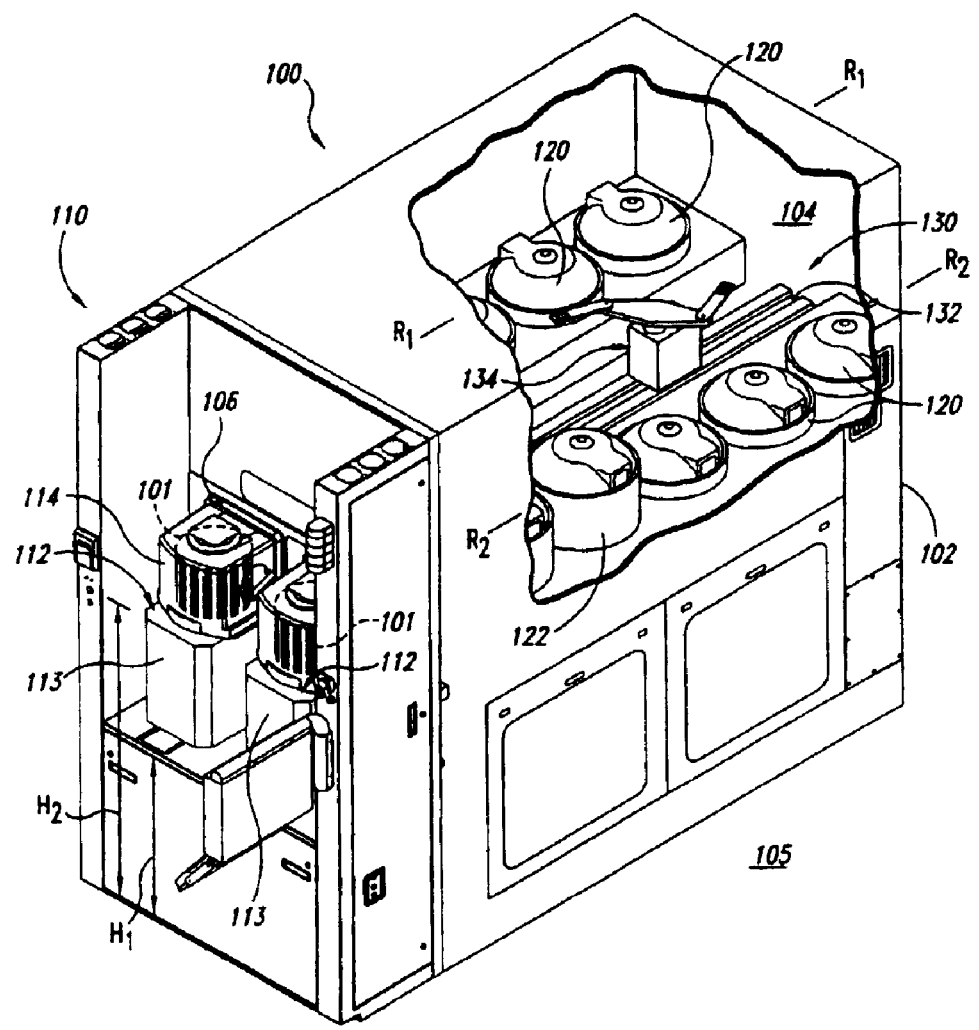
FIG. 2 is an isometric view of an electroprocessing machine having electroprocessing reactors for processing microelectronic workpieces in accordance with an embodiment of the invention.

A. Selected Embodiments of Integrated Tools and Electrochemical Processing Reactors FIG. 2 is an isometric view of a processing machine 100 having electrochemical processing stations 120 in accordance with an embodiment of the invention. A portion of the processing machine 100 is shown in a cut-away view to illustrate selected internal components. In one aspect of this embodiment, the processing machine 100 can include a cabinet 102 having an interior region 104 defining an interior enclosure that is at least partially isolated from an exterior region 105. The cabinet 102 can also include a plurality of apertures 106 (only one shown in FIG. 2) through which microelectronic workpieces 101 can ingress and egress between the interior region 104 and a load/unload station 110.

The load/unload station 110 can have two container supports 112 that are each housed in a protective shroud 113. The container supports 112 are configured to position workpiece containers 114 relative to the apertures 106 in the cabinet 102. The workpiece containers 114 can each house a plurality of microelectronic workpieces 101 in a "mini" clean environment for carrying a plurality of workpieces through other environments that are not at clean room standards. Each of the workpiece containers 114 is accessible from the interior region 104 of the cabinet 102 through the apertures 106.

The processing machine 100 can also include a plurality of clean/etch capsules 122 and a transfer device 130 in the interior region 104 of the cabinet 102. Additional embodiments of the processing machine 100 can include electroless plating stations, annealing stations, and/or metrology stations in addition to or in lieu of the clean/etch capsules 122 and the processing stations 120.

The transfer device 130 includes a linear track 132 extending in a lengthwise direction of the interior region 104 between the processing stations. The transfer device 130 can further include a robot unit 134 carried by the track 132. In the particular embodiment shown in FIG. 2, a first set of processing stations is arranged along a first row $R_1$—$R_1$ and a second set of processing stations is arranged along a second row $R_2$—$R_2$. The linear track 132 extends between the first and second rows of processing stations, and the robot unit 134 can access any of the processing stations along the track 132.

Figure 3:
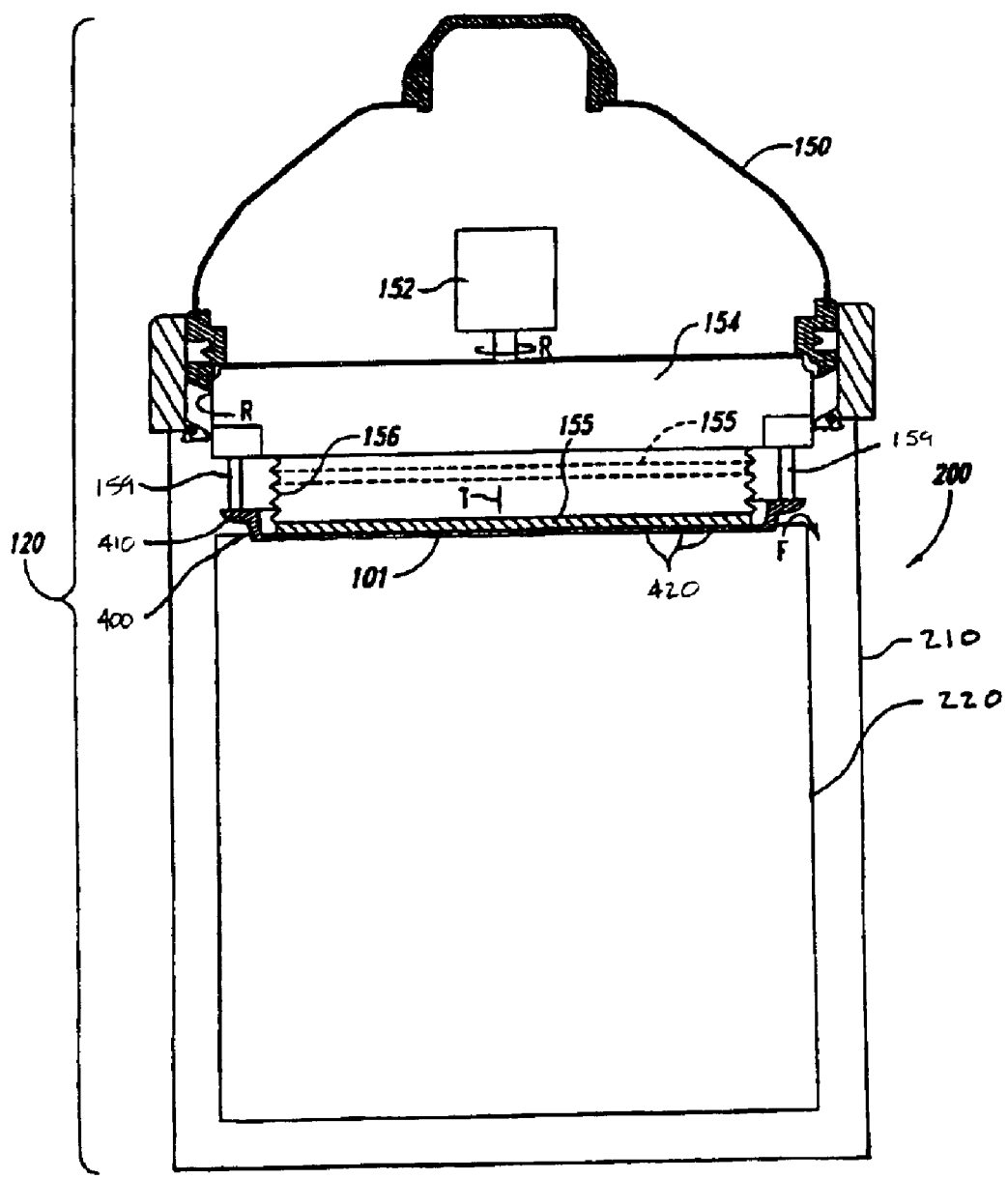
FIG. 3 is a cross-sectional view of an electroprocessing reactor having a head assembly and a processing chamber for use in an electroprocessing machine in accordance with an embodiment of the invention. Selected components in FIG. 3 are shown schematically.

FIG. 3 illustrates an embodiment of an electrochemical processing station 120 having a head assembly 150 and a processing chamber 200. The head assembly 150 includes a spin motor 152, a rotor 154 coupled to the spin motor 152, and a contact assembly 400 carried by the rotor 154. The rotor 154 can have a backing plate 155 and a seal 156. The backing plate 155 can move transverse to a workpiece 101 (arrow T) between a first position in which the backing plate 155 contacts a backside of the workpiece 101 (shown in solid lines in FIG. 3) and a second position in which it is spaced apart from the backside of the workpiece 101 (shown in broken lines in FIG. 3). As described in more detail below with reference to FIGS. 4–11, the contact assembly 400 can have a support member 410 and a plurality of contacts 420 carried by the support member 410. The contact assembly 400 can be removably coupled to the head 150 by a plurality of shafts 159.

The processing chamber 200 can define a reactor that includes an outer housing 210 (shown schematically in FIG. 3) and a reaction vessel 220 (also shown schematically in FIG. 3) in the housing 210. The reaction vessel 220 directs a flow of electroprocessing solution to the workpiece 101. The electroprocessing solution, for example, can flow over a weir (arrow F) and into the housing 210, from which the electroprocessing solution can be recycled.

The head assembly 150 and the contact assembly 400 hold the workpiece 101 at a workpiece-processing site of the reaction vessel 220 so that at least a processing surface of the workpiece engages the electroprocessing solution. An electrical field is established in the solution by applying an electrical potential between the surface of the workpiece via the contact assembly 400 and one or more electrodes located in the processing chamber and/or external to the processing chamber. For example, the contact assembly 400 can be biased with a negative potential with respect to the other electrode(s) to plate metals or other types of materials onto the workpiece. On the other hand, the contact assembly 400 can be biased with a positive potential with respect to the other electrode(s) to (a) de-plate the contacts 420 or electropolish plated material from the workpiece, or (b) deposit other materials onto the workpiece (e.g., electrophoretic resist). In general, therefore, materials can be deposited on or removed from the workpiece with the workpiece acting as a cathode or an anode depending upon the particular type of material used in the electrochemical process.

B. Selected Embodiments of Contact Assemblies and Contacts for Electroprocessing Microelectronic Workpieces FIGS. 4–11 illustrate several embodiments of contact assemblies that can be used in the electroprocessing stations 120 of the machine 100. The structures and operation of the contact assemblies shown in FIGS. 4–11 are generally described with reference to wet-contact assemblies. It will be appreciated, however, that they can also be configured to be dry-contact assemblies. Therefore, the basic structure is applicable to both wet-contact and dry-contact electroprocessing applications.

Figure 4:
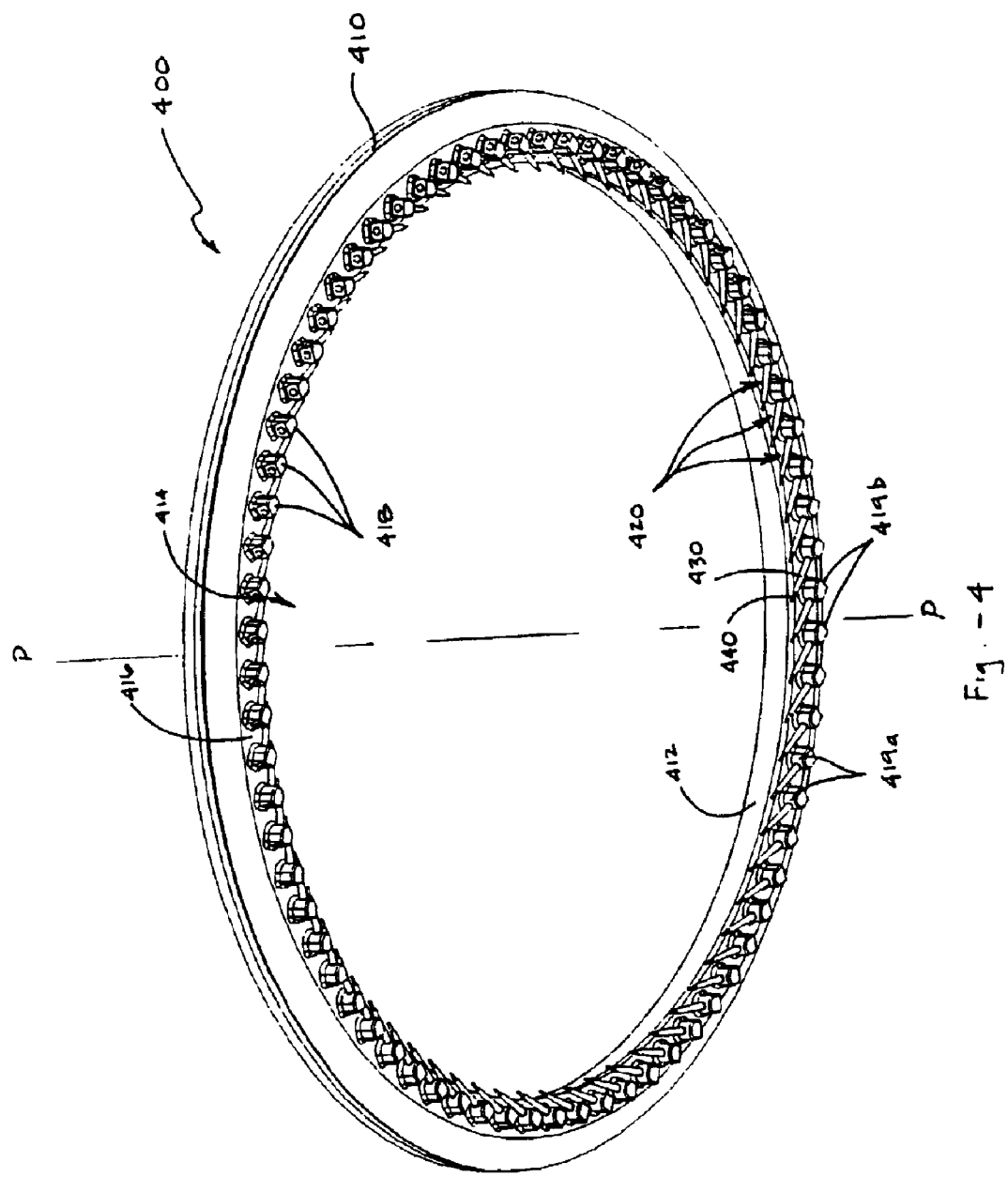
FIG. 4 is a bottom isometric view of a contact assembly in accordance with an embodiment of the invention.
Figure 5:
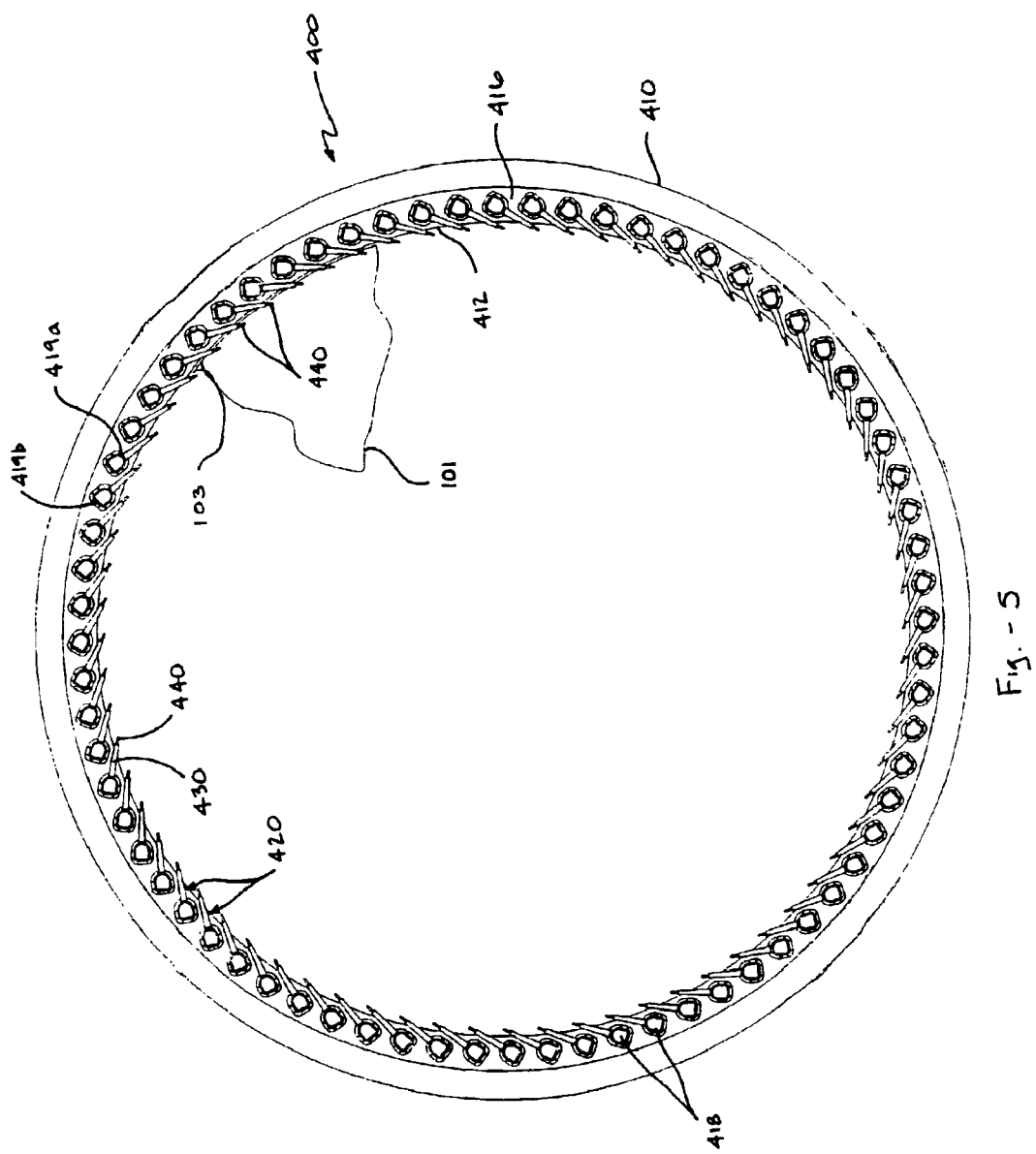
FIG. 5 is a bottom plan view of the contact assembly of FIG. 4.

FIG. 4 is a bottom isometric view and FIG. 5 is a bottom plan view showing the features of an embodiment of a contact assembly 400 in greater detail. In this embodiment, the contact assembly 400 has a support member 410 and a plurality of contacts 420 carried by the support member 410. The support member 410 can have a circular shape, a shape with one or more straight-edge sections, or any other suitable shape corresponding to the shape of the workpiece. The embodiment of the support member 410 shown in FIG. 4 is a ring having an inner wall 412 defining an opening 414 that is configured to allow the workpiece 101 (FIG. 3) to move through the support member 410 along an access path P. The inner wall 412 can be a separate dielectric ring that has a tapered surface with a decreasing diameter to center a workpiece as it passes through the opening 414. The inner wall 412 can alternatively be a tapered wall of a unitary support ring. The opening 414 is accordingly sized just large enough to receive the workpiece. The support member 410 can be formed from a conductive material, such as titanium, stainless steel, or another suitable electrically conductive material. The support member 410 can also have a dielectric coating on the exterior surface of the conductive material. In an alternative embodiment, the support member 410 can be a dielectric ring and a conductive bus in the ring.

In the embodiment shown in FIGS. 4 and 5, the support member 410 includes a bottom surface 416 and a plurality of posts or turrets 418 depending from the bottom surface 416. The turrets 418 are spaced apart from one another by gaps to provide passageways for gas bubbles and electroplating solution to pass through the support member 410 during a processing cycle. The turrets 418 can have several different shapes. For example, the turrets 418 can be substantially rectilinear, cylindrical, oval, or another suitable shape. In the embodiment shown in FIGS. 4 and 5, the turrets have a rounded front face 419a and a linear rear face 419b. The rounded front face 419a of the turrets enhances the ability for a dielectric layer to adhere to the surface of the turrets because plated materials tend to adhere to rounded surfaces better than sharp corners. The linear rear face 419b provides a flat facet to enhance the accuracy of drilling a hole through the turret.

The contacts 420 project inwardly into the opening 414 relative to the support member 410. In the embodiment shown in FIGS. 4 and 5, the contacts 420 are cantilevered members that each have a dielectric cover 430 and a conductor 440 within the cover 430. The exposed tip portion of the conductor 440 defines a contact site on each of the contacts 420. The contacts 420 can project inwardly at an angle relative to the radius of the opening 414 so that they are "swept" as shown in FIGS. 4 and 5. By positioning the contacts 420 to be swept at an angle, the contacts 420 can be quite long to allow more flexure without projecting into the opening 414 much beyond the inner wall 412. This allows the contacts to have a desired flexibility without projecting radially inward beyond a desired peripheral contact area of the workpiece. The swept contact configuration is also expected to reduce flow disturbances radially inward from the distal tip of the contact compared to contacts that project inward along a radius of the support member. Referring to FIG. 5, for example, a section of the workpiece 101 is shown such that an edge 103 of the workpiece 101 is adjacent to the inner wall 412. The distal tip of the conductors 440 contact only a peripheral portion of the workpiece 101 near the edge 103 even though the lengths of the contacts 420 would project much further inward toward the interior of the workpiece 101 if they projected radially inward along a radius of the support member 410. In an alternate embodiment, however, the contacts 420 can project radially inward along a radius of the ring 410 for applications that can use short contacts. Such an alternate embodiment may be useful for applications in which flexing of the contacts is not desirable because shorter contacts will not flex as much as longer contacts.

FIG. 6A is an isometric view and FIG. 6B is a cross-sectional view of a contact 420 in accordance with one embodiment of the invention. The cover 430 can be a dielectric sheath that has a bore 432 (FIG. 6B) and a hole 434. The cover 430, for example, can be a plastic sheath composed of a polyether-etherketone (PEEK), a fluoropolymer (HALAR), or other suitable dielectric materials that are compatible with the particular electrolytic processing solutions. In the embodiment shown in FIGS. 6A and 6B, the cover 430 can include a cylindrical proximal portion 435 and a tapered distal portion 436. The tapered portion 436 can have a smaller cross-section at the distal end so that it does not contact the workpiece before the conductor 440 and to avoid disturbing the fluid flow near the workpiece. The thickness and material of the cover 430 can be selected to make the contact 420 more or less flexible according to the particular application. In alternate embodiments, the cover can be a ceramic material to add rigidity to the contact 420, or the cover can be a coated dielectric layer.

The conductor 440 can be a rod composed of a material that is inert in the particular electrochemical processing solution. The conductor 440, for example, can be a rod composed of platinum, platinum/iridium alloys, stainless steel, tungsten and/or molybdenum. For example, the conductor 440 can be composed of a plantinum/iridium alloy having approximately 10–40% iridium, and more particularly about 15–25% iridium, and still more specifically about 20% iridium. The rods can be solid or tubular. Suitable types of rods include wires having a diameter of 0.010–0.10 inch, and more specifically 0.010–0.030 inch, and still more particularly 0.020 inch. In the particular embodiment shown in FIG. 6B, the conductor 440 has a proximal section 442 received in the bore 432 of the cover 430 and a distal section 443 projecting from the proximal section 442. The distal section 443 has an inert exterior 444 defining a contact site. One aspect of several embodiments of the contact 420 is that the distal section 443 of the conductor 440 has a relatively small cross-sectional area to avoid disturbing the fluid flow at the perimeter of the workpiece. The contact 420 can be formed by molding the cover 430 around the proximal section 442 of the conductor 440. The conductor 440 can alternatively be press fit into the cover 430 so that processing fluid is inhibited from entering the bore 432. Additionally, a viscous sealant can optionally be disposed in the bore 432 to seal the proximal section 442 from processing fluids.

The contacts 420 can also have alternate configurations. In one alternate embodiment, the contacts 420 do not include a dielectric cover such that inert conductors "theive" more material from the processing solution near the perimeter of the workpiece. This embodiment is particularly useful for applications in which it is desirable to reduce the thickness of the plated layer at the perimeter. In other embodiments, the cover 430 can cover more or less of the conductor 440 to further control the degree that the contacts theive material from the electrolytic processing solution.

Figure 6:
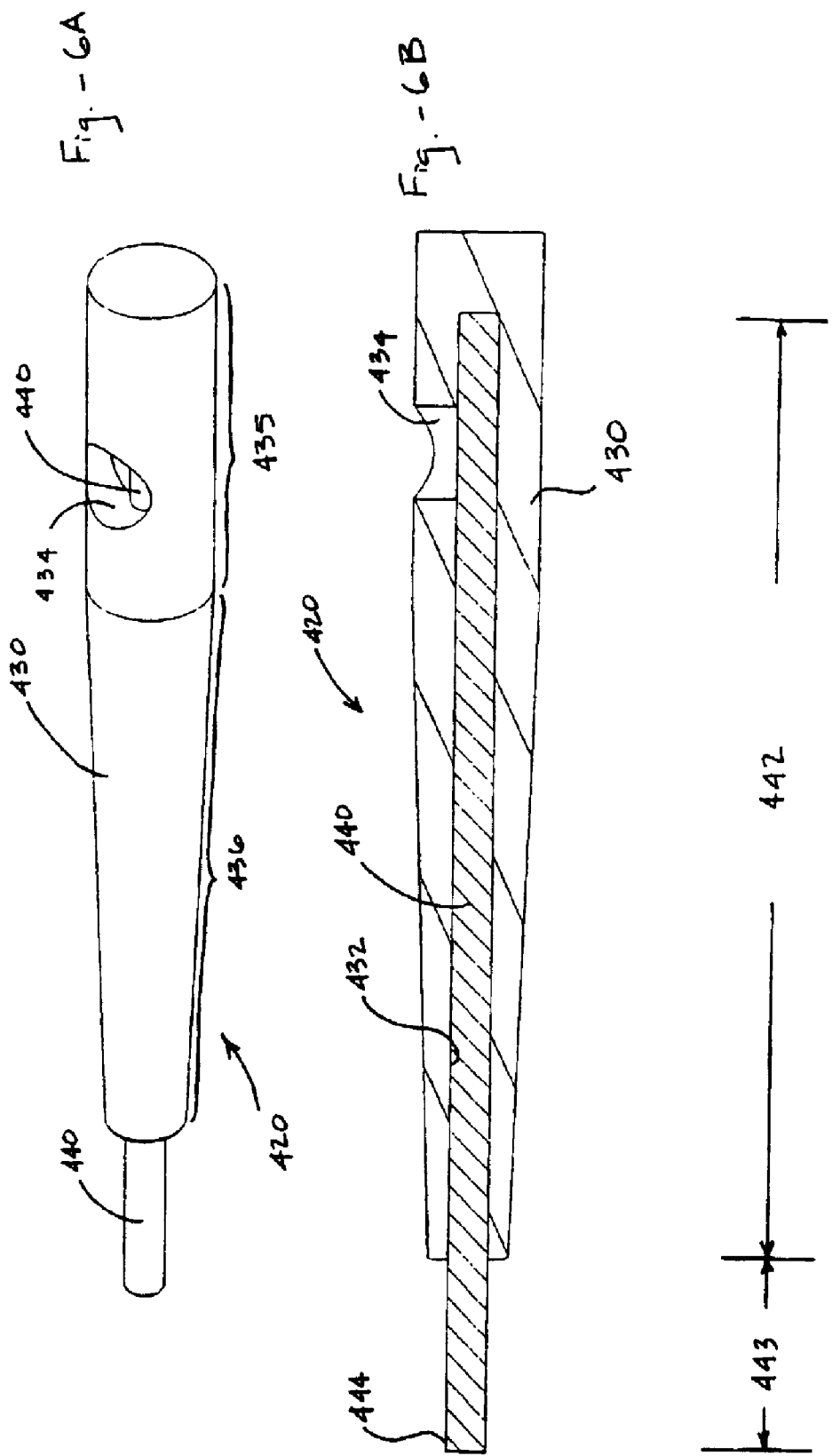
FIG. 6A is an isometric view of a contact for use in a contact assembly in accordance with an embodiment of the invention.
FIG. 6B is a cross-sectional view of the contact of FIG. 6A.
Figure 7:
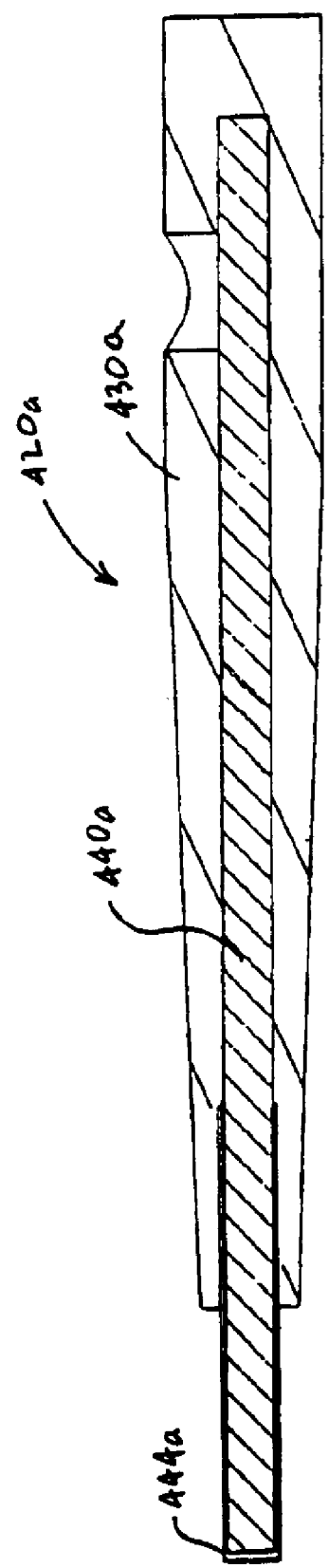
FIG. 7 is a cross-sectional view of a contact for use in a contact assembly in accordance with another embodiment of the invention.

FIG. 7 is a cross-sectional view of another alternate embodiment in which like reference numbers refer to like components in FIGS. 6A–7. In the embodiment shown in FIG. 7, a contact 420a has a conductor 440a with a separate layer of material defining the inert exterior 444a. The cover 430a can include a titanium rod, and the inert exterior 444a can be a platinum layer or any other type of inert material that is plated onto the titanium rod. The contact 420a preferably has a cover 430a that extends distally beyond a proximal portion of the inert exterior 444a. In another embodiment, the inert exterior 444a can completely cover the conductor 440a. The contact 420a can be useful in applications in which the structural integrity of a solid inert conductor is not adequate such that a different type of conductive material is required for the conductor. For example, titanium can be used instead of platinum to increase the rigidity of the contact 420a compared to the contact 420.

Figure 8:
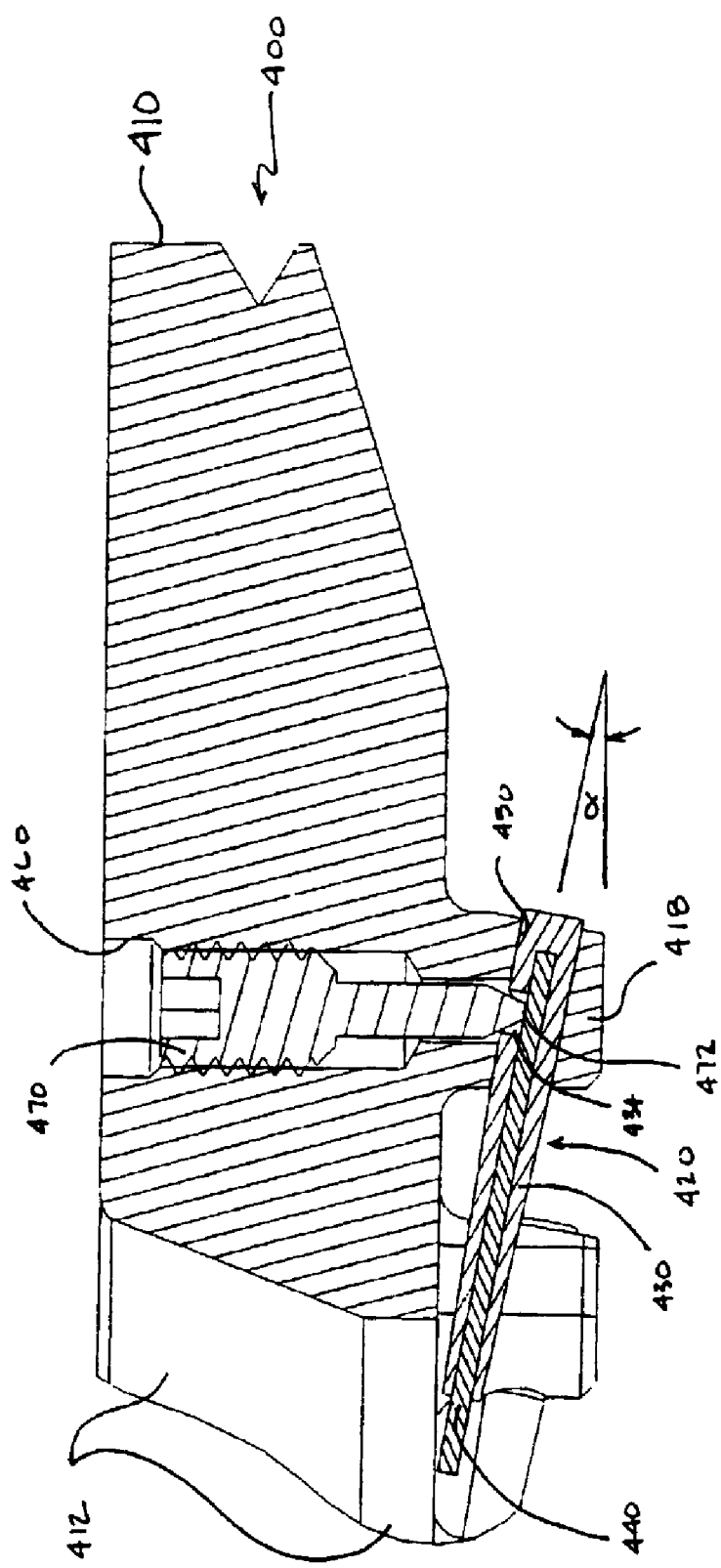
FIG. 8 is a partial cross-sectional view of a contact assembly in accordance with an embodiment of the invention.
Figure 9:
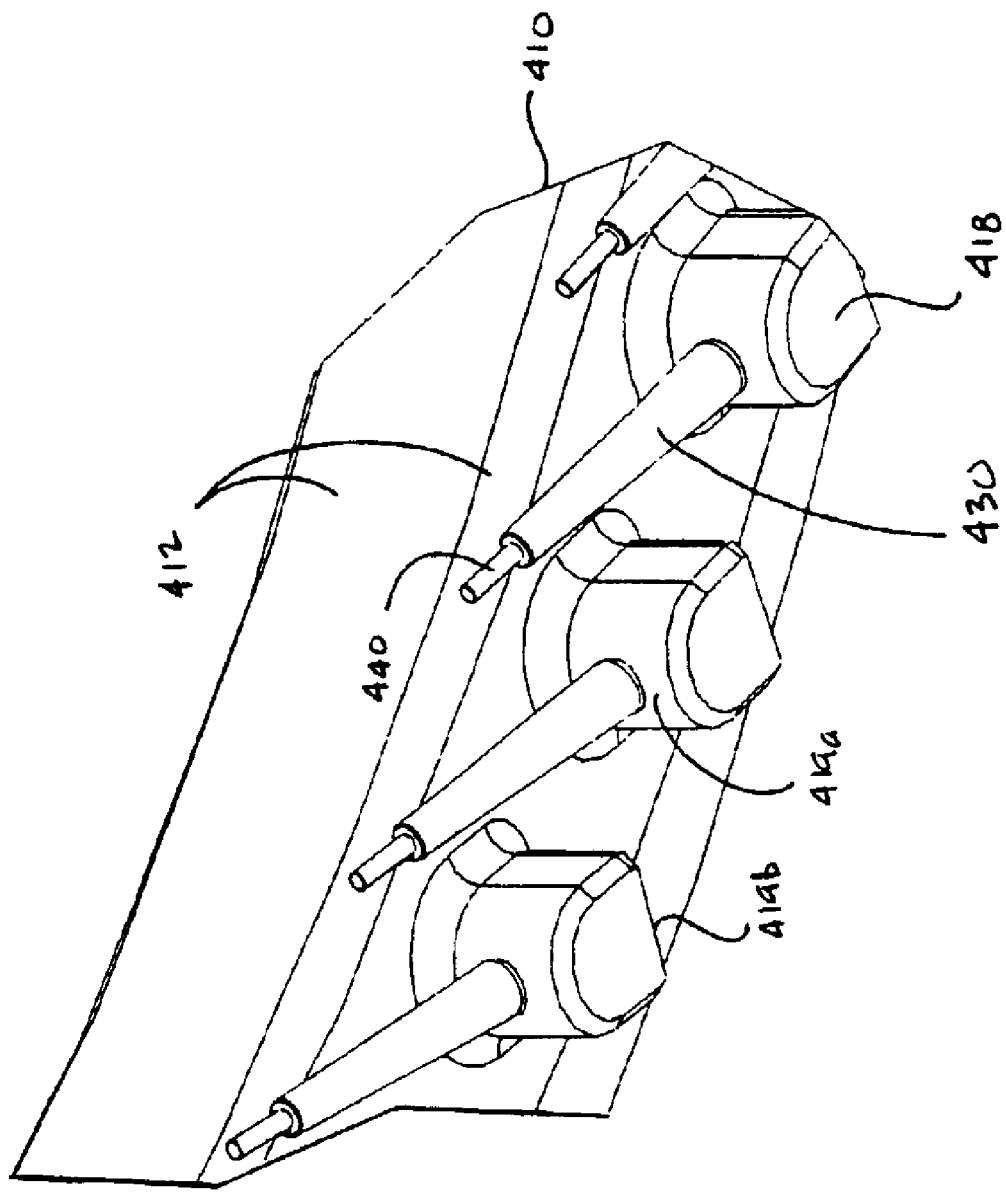
FIG. 9 is a partial isometric view of a contact assembly in accordance with an embodiment of the invention.

FIG. 8 is a partial cross-sectional view and FIG. 9 is a partial bottom isometric view of the contact assembly 400 showing particular features in greater detail. Referring to FIG. 8, the proximal end of the cover 430 is received in a hole 450 in a corresponding turret 418. The hole 450 can extend through the turret 418 at an angle α such that the contact 420 projects inwardly and upwardly relative to the support member 410. In one embodiment, the angle α is approximately 0–15°, and more particularly about 5–10°, and still more specifically about 7–10°. The support member 410 can further include a threaded hole 460 and a set screw 470 having a contact tip 472. The set screw 470 can be composed of titanium and have an external platinum layer, or in other embodiments the set screw 470 can be unplated stainless steel or other suitable conductive materials. The platinum layer can be plated onto the set screw and then annealed in a separate heating operation.

In this embodiment, the support ring 410 is a conductive ring, such as a titanium ring. The conductive ring defines a conductive element. A dielectric layer can be applied to the exterior surfaces of the support member 410. The dielectric coating is generally selected according to (a) the compatibility with the plating solution, (b) adhesion to the metal of the support member 410, and (c) the ability to effectively coat the support member 410. Suitable materials that can be used for the dielectric coating include (a) an 8840 primer and a Teflon dielectric exterior coating manufactured by DuPont® ("DuPont"); (b) an 8840 green coating manufactured by DuPont; (c) a 954–100 epoxy based coating manufactured by DuPont; (d) a 954–101 epoxy based coating manufactured by DuPont; (e) HALAR® coatings under the name Dycore® 404; (f) KYNAR® coatings under the identification Dycore® 202 either with or without a primer of Dycore 204; (g) HALAR® heavy coatings; (h) FLUORO-LON® 109 distributed by Southwest Impreglon® Sales, Inc. of Texas; (I) Impreglon 216® or Impreglon 872® distributed by Southwest Impreglon® Sales, Inc.; and (j) other epoxy based coatings, thermoplastic copolymers, or fluorocarbon resins. In an alternate embodiment, the support member 410 can be a conductive ring without a dielectric coating.

In the particular embodiment shown in FIGS. 8 and 9, the proximal end of the cover 430 is inserted into the hole 450 in the turret 418 so that the hole 434 in the cover 430 is aligned with the set screw 470. The set screw 470 is then threaded into the hole 460 until the contact tip 472 contacts the proximal section of the conductor 440. The set screw 470 accordingly secures the contact 420 to the support member 410 and provides an electrical connection between the support member 410 and the conductor 440. By providing a platinum coating or other inert coating on the set screw 470, or by using a relatively inert set screw 470 (e.g., stainless steel), small amounts of electrolytic processing solution can leak into the hole 434 in the cover without corroding the connection between the set screw 470 and the conductor 440.

Several embodiments of the contact assembly 400 are expected to provide a durable system that has a long life span. One feature that leads to a longer life span is that the conductors 440 are composed of a rod of inert material that is generally much thicker than a plated layer of inert material. This allows the surface of the workpieces to rub against the contacts without affecting the surface on the contacts. This also makes the conductors 440 more robust against corrosion because (a) a different underlying layer of consumable metal cannot be exposed during de-plating cycles, and (b) there are no issues regarding a lack of adhesion between an inert layer and an underlying finger. Therefore, several embodiments of the contact assemblies are expected to have long life spans because of the durability of the contacts 420.

The embodiments of the contact assembly 440 are also expected to be relatively inexpensive to manufacture compared to other types of contact assemblies. One feature that reduces the cost of manufacturing the contact assembly 400 is that the conductors 440 can be solid or tubular pieces of wire formed from an inert material that is easily cut to a desired length, and then a dielectric sheath can be molded around the wire or the wire can be inserted into the sheath. It will be appreciated that this procedure is typically much less expensive compared to procedures that coat a consumable conductive finger with either a thin dielectric layer and/or a thin platinum layer, and then form precise apertures in the dielectric layer. Additionally, another feature of several embodiments of contact assemblies is that individual contacts can be repaired or replaced without having to replace a conductive ring of contacts. As a result, several embodiments of the contact assembly 400 are expected to be relatively inexpensive to manufacture.

FIG. 10A is a partial cross-sectional view of another embodiment of the contact assembly 400 in accordance with the invention. Like reference numbers refer to like components in FIGS. 2–10A. In this embodiment, the contact assembly 400 further includes a boot 500 that has a cavity 510 and an aperture 512. The boot 500 is an elastic dielectric casing that fits over the turret 418 to inhibit processing solution from leaking into the hole 450. The cavity 510 can be sized slightly smaller than the turret 418, and the aperture 512 can be sized slightly smaller than the cover 430. Because the boot 500 is slightly smaller than the turret 418, it provides a good seal around the turret 418. Also, because the aperture 512 is smaller than the diameter of the contact 430, it provides a good seal around the cover 430. FIG. 10B is a top isometric view of an embodiment of the boot 500 attached to the contact assembly 400 in FIG. 10A.

FIG. 11 is a partial isometric view of a contact assembly 600 in accordance with yet another embodiment of the invention. The contact assembly 600 can include a support member 610 and a plurality of movable contacts 620 carried by the support member 610. The support member 610 can be a ring or other shape, and it can have a dielectric exterior coating. The support member 610 can also include an inner wall 612 defining an opening into which the contacts 620 can project. The contacts 620 each include a cover 630 and a conductor 640. The cover 630 can be a dielectric sheath or a dielectric coating. The conductor 640 can be a rod of inert material having a passageway 642 through which a purge gas can flow or a suction can be drawn. The end portion of the conductor 640 extends beyond the cover 630 to provide an electrically conductive contact site for contacting a workpiece. The contacts 620 are attached to the support member 610 by a positionable connection 650 so that the contacts can be swiveled S relative to the support member. The contact assembly 600 accordingly provides a system in which the contacts can be adjusted for varying degree of edge exclusions and patterns, or even different sizes of workpieces. The contact assembly also provides an electrical contact site that can be purged directly at the point of contact by a purge gas.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

What is claimed is:

1. A contact assembly for use in an electrochemical deposition system to apply an electrical potential to a microelectronic workpiece, comprising:

a support member having an inner wall defining an opening configured to receive the workpiece and a plurality of posts projecting from the support member; and a plurality of contacts mounted to the posts, wherein individual contacts include a conductor and a cover, the conductor comprising a proximal section projecting inwardly into the opening relative to the support member, a distal section extending from the proximal section, and an inert exterior at least at the distal section, and the cover comprising a dielectric material covering at least the proximal section of the conductor.

2. The contact assembly of claim 1 wherein:

the support member comprises a conductive ring defining a conductive element and a dielectric exterior;

the cover of an individual contact comprises a dielectric sheath, and wherein the sheath has a bore and projects from a post; and the conductor of the individual contact comprises a rod having a first section received in the bore of the sheath and a second section projecting outside of the sheath.

3. The contact assembly of claim 1 wherein:

the support member comprises a dielectric ring having a conductive bus, and the posts project from the bus;

the cover of a contact comprises a dielectric sheath, and wherein the sheath has a bore and projects from one of the posts; and the conductor of the contact comprises a rod having a first section received in the bore of a cover and a second section projecting outside of the sheath, and wherein the rods are electrically coupled to the conductive bus in the ring.

4. The contact assembly of claim 1 wherein:

the support member comprises a ring having a conductive element coupled to the posts;

the cover of a contact comprises a dielectric sheath, and wherein the sheath has a bore and projects from one of the posts at an angle swept relative to a radius of the ring; and the conductor of the contact comprises a rod having a first section received in the bore and a second section projecting outside of the sheath.

5. The contact assembly of claim 1 wherein:

the support member comprises a ring having a conductive element coupled to the posts;

the cover of a contact comprises a dielectric sheath, and wherein the sheath has a bore and projects inwardly and upwardly from one of the posts; and the conductor of the contact comprises a rod having a first section received in the bore and a second section projecting outside of the sheath.

6. The contact assembly of claim 1 wherein:

the cover of a contact comprises a dielectric sheath, and wherein the sheath has a bore and projects inwardly into the opening; and the conductor of the contact comprises a rod having a first section received in the bore and a second section projecting from the sheath.

7. The contact assembly of claim 1 wherein a plurality of boots cover corresponding posts.

8. The contact assembly of claim 1 wherein the conductor of an individual contact has an aperture through which a gas can flow.

9. The contact assembly of claim 1 wherein the contacts are coupled to the support member by positionable connectors that allow the contacts to swivel with respect to the support member.

10. The contact assembly of claim 1 wherein the cover comprises a dielectric sheath having a bore.

11. The contact assembly of claim 1 wherein the conductor comprises a rod composed of platinum or a platinum/iridium alloy.

12. The contact assembly of claim 1 wherein the conductor comprises a titanium rod having a platinum coating.

13. The contact assembly of claim 1 wherein the conductor comprises a stainless steel rod.

14. The contact assembly of claim 1 wherein the conductor comprises a tungsten rod.

15. The contact assembly of claim 1 wherein the conductor comprises a tungsten rod having a platinum coating.

16. A contact assembly for use in an electrochemical deposition system to apply an electrical potential to a microelectronic workpiece, comprising:

a support member having an inner wall defining an opening configured to receive the workpiece, a dielectric exterior, and an electrically conductive element within the dielectric exterior, the support member comprises a ring and a plurality of turrets; and a contact system having a plurality of contacts projecting inwardly into the opening relative to the support member, the contacts including a conductor having a contact site with an inter surface and a dielectric cover over at least a portion of the conductor, and the conductor being electrically couple to the conductive element of the support member, wherein the covers of the contacts comprise dielectric sheaths, and wherein the sheaths have a bore and project from the turrets at an angle swept relative to a radius of the ring; and the conductors of the contacts comprise rods having a proximal section received in the bore of a cover and a distal end projecting outside of the cover.

17. A contact assembly for use in an electrochemical deposition system to apply an electrical potential to a microelectronic workpiece, comprising:

a ring having an inner wall defining an opening configured to receive the workpiece, wherein the ring has a conductive element, a dielectric exterior, and a plurality of turrets; and a plurality of contacts projecting inwardly from the ring into the opening, the contacts comprising a dielectric element and a conductor having a first section in the dielectric element and a second section exposed relative to the dielectric element, wherein at least the second section of the conductor has an inert exterior, and wherein the dielectric elements comprise sheaths that have a bore and project from the turrets; and the conductors of the contacts comprise rods having a proximal section received in the bore of a cover and a distal end projecting inwardly from the cover.

18. The contact assembly of claim 17 wherein:

the sheaths project from the turrets at an angle swept relative to a radius of the ring; and the rods are partially received in the sheaths.

19. The contact assembly of claim 17 wherein:

the sheaths project inwardly and upwardly from the turrets; and the rods are partially received in the sheaths.

20. A contact assembly for use in an electrochemical deposition system to apply an electrical potential to a microelectronic workpiece, comprising:

a ring having an inner wall defining an opening configured to receive the workpiece, wherein the ring has a dielectric body, a conductive bus carried by the body, and a plurality of turrets;

the dielectric elements comprise sheaths that have a bore and project from the turrets; and the conductors of the contacts comprise rods having a proximal section received in the bore of a sheath and a distal end projecting inwardly from the sheath, and wherein the rods are electrically coupled to the conductive bus in the ring.

21. A contact assembly for use in an electrochemical deposition system to apply an electrical potential to a microelectronic workpiece, comprising:

a support member having a ring including an inner wall defining an opening configured to receive the workpiece and a plurality of turrets depending downwardly;

a plurality of dielectric sheaths coupled to the support member, wherein each sheath has a bore and projects from a corresponding turret inwardly into the opening; and a plurality of conductors having a first section, a second section, and an inert exterior on at least the second section, wherein at least the first section of each conductor is received in the bore of a sheath.

22. The contact assembly of claim 21 wherein the conductors comprise platinum rods.

23. The contact assembly of claim 21 wherein the conductors comprise titanium rods having a platinum coating.

24. The contact assembly of claim 21 wherein the conductors comprise stainless steel rods.

25. The contact assembly of claim 21 wherein the conductors comprise tungsten rods.

26. A reactor for electrochemical deposition processing of a microelectronic workpiece, comprising:

a vessel configured to hold a processing solution;

an electrode disposed relative to the vessel to provide an electrical potential in the vessel;

a head assembly moveable relative to the vessel between a load/unload position and a processing position; and a contact assembly carried by the head assembly, wherein the contact assembly comprises a support member having an inner wall defining an opening configured to receive the workpiece and a plurality of posts projecting from the support member; and a plurality of contacts mounted to the posts, wherein individual contacts include a conductor and a cover, the conductor comprising a proximal section projecting inwardly into the opening relative to the support member, a distal section extending from the proximal section, and an inert exterior at least at the distal section, and the cover comprising a dielectric element covering at least the proximal section of the conductor.

27. The reactor of claim 26, wherein the support member comprises a ring having a conductive element and the posts comprise turrets; and the contacts further comprise rods and dielectric sheaths along a proximal portion of the rods.

28. A reactor for electrochemical deposition processing of a microelectronic workpiece, comprising:

a vessel configured to hold a processing solution;

an electrode disposed relative to the vessel to provide an electrical potential in the vessel;

a head assembly moveable relative to the vessel between a load/unload position and a processing position; and a contact assembly carried by the head assembly, wherein the contact assembly comprises a support member having a ring including an inner wall defining an opening configured to receive the workpiece and a plurality of turrets depending downwardly;

a plurality of dielectric sheaths coupled to the support member, wherein each sheath has a bore and projects from a corresponding turret inwardly into the opening; and a plurality of conductors having a first section, a second section, and an inert exterior on at least the second section, wherein at least the first section of each conductor is received in the bore of a sheath.

29. The reactor of claim 28 wherein the conductors comprise platinum rods.

30. The reactor of claim 28 wherein the conductors comprise titanium rods having a platinum coating.

31. The reactor of claim 28 wherein the conductors comprise stainless steel rods.

32. The reactor of claim 28 wherein the conductors comprise tungsten rods.

33. A tool for electrochemical processing of a microelectronic workpiece, comprising:

a cabinet;

a transfer mechanism; and an electroplating reactor in the cabinet comprising a vessel configured to hold a processing solution, an electrode disposed relative to the vessel to provide an electrical potential in the vessel, a head assembly moveable relative to the vessel between a load/unload position and a processing position, and a contact assembly carried by the head assembly, wherein the contact assembly comprises a support member having an inner wall defining an opening configured to receive the workpiece and a plurality of posts projecting from the support member; and a plurality of contacts mounted to the posts, wherein individual contacts have a conductor and a cover, the individual conductors comprising a proximal section projecting inwardly into the opening relative to the support member, a distal section extending from the proximal section, and an inert exterior at least at the distal section, and the individual covers comprising a dielectric material covering at least the proximal section of a corresponding individual one of the conductors.

34. The tool of claim 33 wherein:

the support member comprises a ring having a conductive element, a dielectric exterior, and the posts comprise turrets; and the conductors further comprise rods.

35. The tool of claim 34 further comprising dielectric sheaths covering proximal sections of the rods.

36. The tool of claim 33 the conductors comprise platinum rods.

37. The tool of claim 33 wherein the conductors comprise titanium rods having a platinum coating.

38. The tool of claim 33 wherein the conductors comprise stainless steel rods.

39. The tool of claim 33 wherein the conductors comprise tungsten rods.

40. A tool for electrochemical processing of a microelectronic workpiece, comprising:

a cabinet;

a transfer mechanism; and an electroplating reactor in the cabinet comprising a vessel configured to hold a processing solution, an electrode disposed relative to the vessel to provide an electrical potential in the vessel, a head assembly moveable relative to the vessel between a load/unload position and a processing position, and a contact assembly carried by the head assembly, wherein the contact assembly comprises a support member having a ring including an inner wall defining an opening configured to receive the workpiece and a plurality of turrets depending downwardly;

a plurality of dielectric sheaths coupled to the support member, wherein each sheath has a bore and projects from a corresponding turret inwardly into the opening; and a plurality of conductors having a first section, a second section, and an inert exterior on at least the second section, wherein at least the first section of each conductor is received in the bore of a sheath.

41. The tool of claim 40 wherein the conductors comprise platinum rods.

42. The tool of claim 40 wherein the conductors comprise titanium rods having a platinum coating.

43. The tool of claim 40 wherein the conductors comprise stainless steel rods.

44. The tool of claim 40 wherein the conductors comprise tungsten rods.

* * * * *